United States Patent [19]
Baba et al.

[11] Patent Number: 5,596,018
[45] Date of Patent: Jan. 21, 1997

[54] ANTIVIRAL AGENTS AGAINST AIDS-CAUSING VIRUS

[75] Inventors: Masanori Baba, Fukushima, Japan; Dominique Schols, Herent, Belgium; Rudi Pauwels, Weerde, Belgium; Jan Balzarini, Heverlee, Belgium; Erik De Clercq, Lovenjoel, Belgium

[73] Assignee: Toray Industries, Inc., Tokyo, Japan

[21] Appl. No.: 110,322

[22] Filed: Aug. 20, 1993

Related U.S. Application Data

[63] Continuation of Ser. No. 566,450, filed as PCT/JP89/00992, Sep. 29, 1989, abandoned.

[30] Foreign Application Priority Data

Dec. 28, 1988 [JP] Japan .................... 63-332327

[51] Int. Cl.⁶ ............................................. A61K 31/185
[52] U.S. Cl. ................................................ 514/576
[58] Field of Search ................................. 514/576

[56] References Cited

U.S. PATENT DOCUMENTS 4,277,492 7/1981 Daniel et al. .................... 424/304

FOREIGN PATENT DOCUMENTS 4117025 2/1978 Japan ...................... A01N 9/14

OTHER PUBLICATIONS

Biochemical and Biophysical Research Communications, "Fuchsin Acid Selectively Inhibits Human Immunodeficiency", Sep. 30, 1988, pp. 1404–1411 (vol. 155, No. 3 1988).

Merck Index 10th Ed #4155.

*Primary Examiner*—Russell Travers
*Attorney, Agent, or Firm*—Austin R. Miller

[57] ABSTRACT

An antiviral agent against viruses causative of AIDS, containing fuchsinic acid as an active ingredient.

The antiviral agents provided by the present invention inhibit cellular infection by AIDS-causing virus and progress of the infection into ARC and are effective in the treatment of AIDS.

4 Claims, 1 Drawing Sheet

ANTIVIRAL AGENTS AGAINST AIDS-CAUSING VIRUS

This application is a continuation of application Ser. No. 07/566,450, now abandoned, filed as PCT/JP89/00992 Sep. 29, 1989..

FIELD OF THE INVENTION

This invention relates to an antiviral agent effective against a virus causing AIDS for which no definitive treatment has been known.

BACKGROUND OF THE INVENTION

Known agents possessing an antiviral activity include those compounds which may inhibit viral DNA synthesis, such as ara-A and acyclovir, an those which may inhibit reverse transcriptases of retroviruses, such as suramin, ribavirin and AZT (azidothymidine).

Retroviruses are RNA viruses of which RNA is transcribed into DNA with reverse transcriptase. The etiologic agent causing acquired immunodeficiency syndrome (AIDS) is a retrovirus called HTLV-III (human T-cell lymphotrophic virus type III), LAV (lymphadenopathy-associated virus) or HIV (human immunodeficiency virus).

AIDS develops in the form of Kaposi's sarcoma and opportunistic infections such as *Pneumocystis carinii* pneumonia (PCP), candidiasis, aspergillosis and amebic colitis, which arise due to a depressed immune response of a living body. AZT is the only drug known as an agent capable of inhibiting the growth of HIV.

When infected with the AIDS-causing virus, the subject becomes an asymptomatic carrier (AC), then develops AIDS related complex (ARC) and eventually overt symptoms of AIDS.

Those antiviral agents which act as inhibitors of viral reverse transcriptases are fairly toxic to normal cells and have marked side effects on patients, thus leading to debility of body besides prolongation of life upon administration.

An object of this invention is to provide antiviral agents effective in suppressing cellular infection of AIDS-causing virus and/or inhibiting further progress of the infection into ARC and into AIDS, hence useful in the treatment of AIDS, by means of a low toxic substance which may inhibit reverse transcriptases and have other mechanisms of action.

DISCLOSURE OF THE INVENTION

The present invention comprises antiviral agents against virus causative of AIDS, containing fuchsinic acid as an active ingredient.

BEST MODE OF MAKING THE INVENTION

Fuchsinic acid used in the present invention is an anionic dye with the following chemical structure.

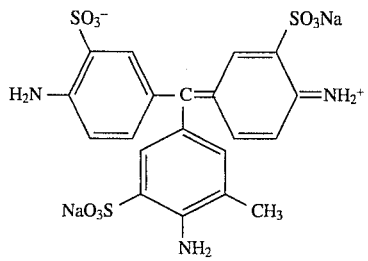

Since its antiviral activity against HIV was observed at a concentration of 16 μM, said compound may also be believed to be effective against the virus at similar concentrations in human blood. Thus, the dosage of the compound may be expected to range from 2 mg to 1 g per 60 kg of body weight.

The antiviral agents may further contain stabilizers and other ingredients and may be used in various dosage forms such as injection, capsules, intranasal preparations, suppositories, oral preparations and ointments.

EXAMPLES (A) Human T4 Lymphocyte Line

Anti-HIV assays of fuchsinic acid were carried out in cultures of MT-4 and HUT-78 cells infected with AIDS-causing viruses such as HIV type 1 (HIV-1) and HIV type 2 (HIV-2), taking cytopathogenicity as a parameter of the inhibitory effect on replication of the viruses. The anti-HIV activity was also measured by monitoring the expression of viral antigen.

Furthermore, cytotoxicity assay of fuchsinic acid was performed by the method of Balzarini et al. [Balzarini, J., DeClercq, E., Torrence, P. F., Mertes, M. P., Park, J. S., Schmidt, C. L., Shugar, D., Barr, P. J., Jones, A. S., Verhelst, G. and Walker, R. T. (1982) *Biochem. Pharmacol.*, 31, 1089–1095; and Balzarini, J., Mitsuya, H., DeClercq, E. and Broder, S. (1986) *Biochem, Biophys Res. Commun.*, 136, 64–71] using L1210, FM3A, Raji, Molt/4F and CEM cell lines.

Assessments were also made as to reverse transcriptase and viral adsorption.

(B) Effect of fuchsinic acid on cells infected by AIDS-causing viruses

Experiments to assess the inhibitory effect of fuchsinic acid on HIV-1, an AIDS-causing virus, demonstrated that said compound produced complete inhibition of cytopathogenic effect (CPE) at a concentration of 125 μM (FIG. 1-A) with a 50% effective dose ($ED_{50}$) of 42 μM (Table 1). The $ED_{50}$ was 63 μM for HIV-2. HIV-1 antigen was inhibited at 25 μM, with $ED_{50}$ being 16 μM (Table 1).

TABLE 1

| | Anti-HIV effect of fuchsinic acid in MT-4 and HUT-78 cells | | | |
|---|---|---|---|---|
| Compound | Cell | $ED_{50}^a$ (μM) | $ED_{50}^b$ (μM) | SI[c] |
| Fuchsinic acid | MT-4 | 42 | >3125 | <74 |
| | HUT-78 | 16 | >625 | <39 |
| ATA[d] | MT-4 | 5.0 | 590 | 118 |

TABLE 1-continued

Anti-HIV effect of fuchsinic acid in MT-4 and HUT-78 cells

| Compound | Cell | $ED_{50}^a$ (μM) | $ED_{50}^b$ (μM) | $SI^c$ |
|---|---|---|---|---|
| | HUT-78 | 0.69 | 13 | 19 |
| Suramin | MT-4 | 32 | 625 | 20 |
| | HUT-78 | 18 | 55 | 3.1 |
| Aurin | MT-4 | >2.6 | 2.6 | <1 |
| | HUT-78 | >2.3 | 2.3 | <1 |

Figure 1A:
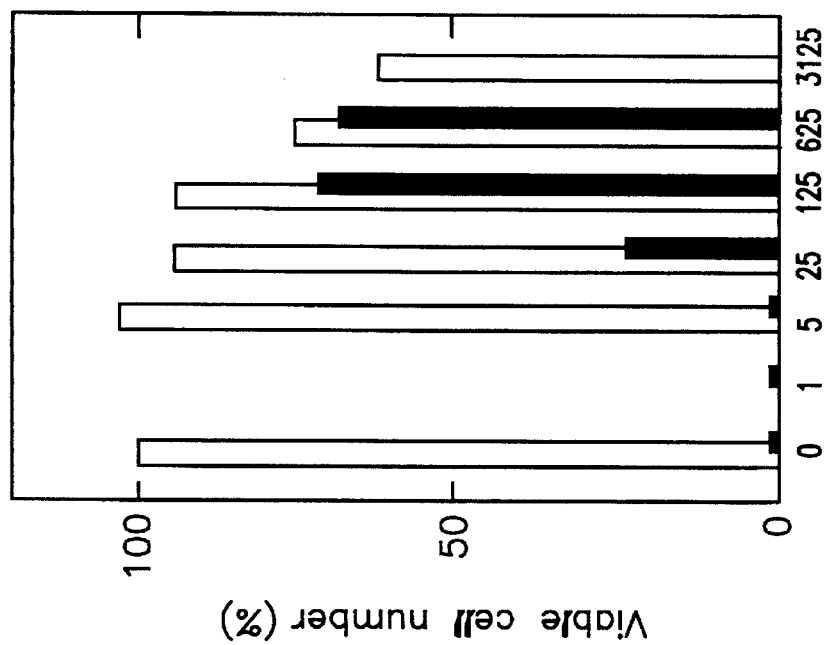
FIG. 1A depicts the inhibitory effect of fuchsinic acid on cytopathogenicity: ■; virus-infected MT-4 cells, and □; MT-4 cells (control).
Figure 1B:
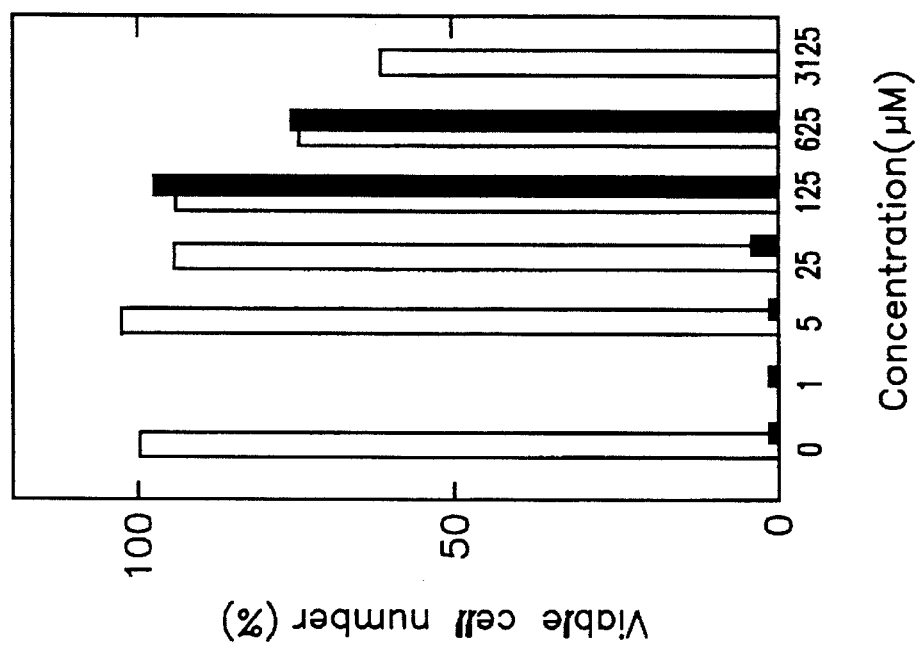
FIG. 1B depicts the inhibitory effect of fuchsinic acid on cytopathogenicity: ■; HIV-2 virus-infected MT-4 cells, and □; MT-4 cells (control).

[a]: Antiviral 50% effective dose
[b]: 50% cytopathogenicity
[c]: Selective index
[d]: Aurintricarboxylic acid FIG. 1 shows the inhibitory effect of fuchsinic acid on viral cytopathogenicity. Panel A shows data for HIV-1 in MT-4 cells and panel B for HIV-2 in MT-4 cells.

Inhibitory effect of fuchsinic acid on reverse transcriptase of HIV-1 is illustrated in FIG. 2.

Applicability in Industry

The antiviral agents provided by this invention are effective in inhibiting cellular infection by AIDS-causing virus and progress of the infection into ARC and in the treatment of AIDS.

Since said agent may also exert an antiviral effect against HIV-2, it may also be expected to be effective for tumors of the hematopoietic organs such as adult T cell leukemia (ATL) and hairly cell leukemia where retroviruses have been incriminated as etiologically responsible. The agent is also effective in viral hepatitis B and in non-A non-B hepatitis.

We claim:

1. A method of inhibiting HIV comprising contacting HIV infected cells with an effective amount of fuchsinic acid.

2. The method of claim 1 wherein said fuchsinic acid has the formula:

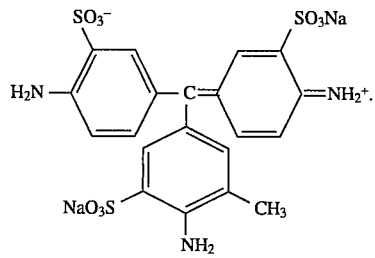

3. A method of inhibiting HIV comprising contacting HIV-infected human cells with an effective amount of fuchsinic acid.

4. The method of claim 3 wherein said fuchsinic acid has the formula:

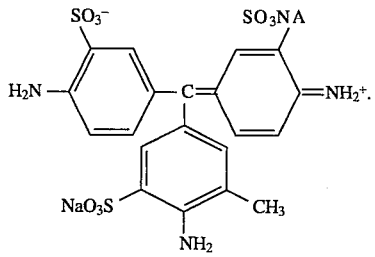

* * * * *